United States Patent [19]

Abendschein

[11] Patent Number: 5,824,644
[45] Date of Patent: Oct. 20, 1998

[54] METHOD OF ATTENUATING ARTERIAL STENOSIS

[75] Inventor: Dana R. Abendschein, St. Louis, Mo.

[73] Assignee: G. D. Searle & Co., Chicago, Ill.

[21] Appl. No.: 675,122

[22] Filed: Jul. 3, 1996

Related U.S. Application Data

[63] Continuation-in-part of Ser. No. 648,777, May 16, 1996, abandoned, which is a continuation-in-part of Ser. No. 271,930, Jul. 7, 1994, abandoned.

[51] Int. Cl.$^6$ .......................... A61K 38/00; C07K 14/00; A61F 13/00
[52] U.S. Cl. ................. 514/12; 514/2; 514/21; 530/324; 530/350; 530/380; 424/422
[58] Field of Search .................. 514/12, 2, 21; 530/350, 324, 380; 424/422

[56] References Cited

U.S. PATENT DOCUMENTS

| | | | |
|---|---|---|---|
| 4,258,192 | 3/1981 | Okamoto et al. | 546/166 |
| 4,966,852 | 10/1990 | Wun et al. | 435/235 |
| 5,106,833 | 4/1992 | Broze et al. | 514/12 |
| 5,212,091 | 5/1993 | Diaz-Collier et al. | 435/69.6 |
| 5,219,994 | 6/1993 | Buonassisi et al. | 530/380 |
| 5,276,015 | 1/1994 | Wun | 514/12 |
| 5,308,622 | 5/1994 | Cascells et al. | 424/422 |
| 5,312,736 | 5/1994 | Rasmussen et al. | 435/69.2 |
| 5,326,757 | 7/1994 | Demopoulos et al. | 514/167 |
| 5,378,732 | 1/1995 | Horrobin et al. | 514/560 |
| 5,385,935 | 1/1995 | Tamaii et al. | 514/535 |
| 5,409,894 | 4/1995 | Handley et al. | 514/8 |
| 5,422,362 | 6/1995 | Vincent et al. | 514/410 |
| 5,441,947 | 8/1995 | Dodge et al. | 514/179 |
| 5,480,888 | 1/1996 | Kodama et al. | 514/310 |
| 5,488,058 | 1/1996 | Palkowitz | 514/324 |
| 5,523,292 | 6/1996 | Schwartz et al. | 514/21 |

FOREIGN PATENT DOCUMENTS

WO 93/24143 12/1993 WIPO.
WO 93/25230 12/1993 WIPO.

OTHER PUBLICATIONS

Broze and Miletich, Proc. Natl. Acad. Sci. USA 84, 1886–1890 (1987).
Novotny et al., J. Biol. Chem. 264, 18832–18837 (1989).
Wun et al., J. Biol. Chem. 265, 16096–16101 (1990).
Wun et al., J. Biol. Chem. 263, 6001–6004 (1988).
Girard et al., Thromb. Res. 55, 37–50 (1989).
Girard et al., Nature 328, 518–520 (1989).
Rapaport, Blood 73, 259–365 (1989).
Broze et al., Biochemistry 29, 7539–7546 (1990).
Day et al., Blood 76, 1538–1545 (1990).
Pedersen et al., J. Biol. Chem. 265, 16786–16793 (1990).
Wun et al., Thromb. Hemostas. 68, 54–59 (1992).
Sprecher et al., Proc. Natl. Acad. Sci. USA 91, 3353–3357 (1994).
Diaz–Collier, Thromb. Hemostas. 71, 339–346 (1994).
Gustafson et al; Prot. Express. Purif. 5,233–241 (1994).
Abendschein et al; Circulation 92, 944–949 (1995).
Speidel et al; Circulation 92, 3323–3330 (1995).
Haskel et al, *Circulation*, vol. 84, No. 2, pp. 821–827, Aug. 1991.

*Primary Examiner*—Cecilia J. Tsang
*Assistant Examiner*—Abdel A. Mohamed
*Attorney, Agent, or Firm*—Dennis A. Bennett

[57] ABSTRACT

A method is disclosed for attenuating stenosis after balloon angioplasty. The method comprises administering to a host parenterally or locally to the luminal surface of the blood vessel subjected to said balloon angioplasty an effective amount of tissue factor pathway inhibitor (TFPI) for a prolonged period of time sufficient to substantially reduce the extent of restenosis. An exemplary amount of the TFPI is from about 0.5 mg/kg to about 6 mg/kg during a prolonged administration of about twelve (12) hours to 36 hours.

14 Claims, 11 Drawing Sheets

METHOD OF ATTENUATING ARTERIAL STENOSIS

CROSS-REFERENCE TO RELATED APPLICATION

This is a continuation-in-part of application Ser. No. 08/648/777, filed May 16, 1996, now abandoned, which is a continuation of application Ser. No. 08/271,930, filed Jul. 7, 1994, now abandoned.

This invention was made in part with government support under grant number HL 17646 awarded by the National Institutes of Health. The government has certain rights in the invention.

BACKGROUND OF THE INVENTION

This invention relates to a novel method of attenuating arterial stenosis. More particularly, the invention relates to a method of reducing or inhibiting restenosis following balloon angioplasty by the administration of a blood coagulation inhibitor known as lipoprotein-associated coagulation inhibitor (LACI) and alternatively as tissue factor pathway inhibitor (TFPI).

Balloon angioplasty is a widely used medical procedure for treatment of arterial blockage. However, early thrombotic reocclusion of treated arteries occurs in approximately 5% of patients as reported by Ip et al., *J.Am.Col.Cardiol.* 17, 77B–88B (1991). Furthermore, stenosis, which is a narrowing or stricture of the artery, reoccurs within three (3) months in up to 50% of arteries successfully recanalized by angioplasty as reviewed by Ip et al., *J.Am.Col.Cardiol.* 17, 77B–88B (1991), and by Franklin et al., *Coronary Artery Dis.* 4, 232–42 (1993). The reocclusion and restenosis following balloon angioplasty thus necessitates repeat angioplasty in many patients as described by Holmes et al., *Am.J.Cardiol.* 53, 77C (1984), and Lincoff et al., *J.Am.Col.Cardiol.* 19, 926–35 (1992).

Overall, the efficacy of coronary revascularization procedures such as balloon angioplasty in patients with coronary artery disease is limited by a 30 to 50% incidence of restenosis that occurs within six (6) months after the intervention. Landau et al., *New Engl. J. Med.* 330, 981–993 (1994). Accordingly, a method of attenuating stenosis after balloon angioplasty would have significant utility in medical practice.

Anticoagulation treatment with intravenous heparin is standard clinical practice to inhibit thrombosis during and after angioplasty. Despite its effect to inhibit thrombin, and evidence that it may inhibit smooth muscle cell proliferation, however, heparin does not appear to attenuate restenosis in patients as reported by Ellis et al., *Am. Heart J.* 117, 777–82 (1989).

Similarly, in experimental animals, Gimple et al. reported (*Circulation* 86, 1536–46, 1992) that chronic, subcutaneous administration of heparin did not improve the absolute luminal diameter after balloon angioplasty. See also Laskey et al., *Am. J. Cardiol.* 65, 179–182 (1990). Even potent, direct inhibition of thrombin with hirudin administered during and for several days after angioplasty in patients has failed to prevent restenosis. Serruys et al., *New Engl. J. Med.* 333, 757–763 (1995).

Other anticoagulants have been tested to inhibit restenosis, but the results are inconclusive. Administration of the oral anticoagulant warfarin did not decrease rates of restenosis in patients as described by Thornton et al., *Circulation* 69, 721–7 (1984), and Urban et al., *Br. Heart J.* 60, 485–8 (1988). Direct inhibition of thrombin with recombinant desulfatohirudin administered for only two (2) hours after angioplasty of iliac arteries in rabbits decreased luminal stenosis one month later according to Sarembock et al., *Circulation* 84, 232–43 (1991). However, Webster et al. (*Circulation* 84, II580, 1991) showed that the same inhibitor infused continuously for two (2) weeks after balloon-induced arterial injury in pigs did not attenuate subsequent luminal stenosis. Nevertheless, inhibition of factor $X_a$ with low molecular weight heparin was shown to decrease intimal proliferation following balloon angioplasty in rabbits as reported in Hanke et al., *Circulation* 85, 1548–56 (1992).

Recently, it has been shown that administration of recombinant hirudin in dosages that increased partial thromboplastin time >2-fold for three (3) hours after balloon-induced injury to carotid or coronary arteries in minipigs markedly decreased neointimal formation and luminal stenosis within one month later. Abendschein et al., *J. Am. Coll. Cardiol.*, In press; Unterberg et al., *Ibid.* 26, 1747–1754 (1995).

However, frequent bleeding complications observed in patients given more modest dosages of hirudin implies that higher dosing levels will not be acceptable for clinical use. Antmen, *Circulation* 90, 1624–1630 (1994).

It is thus evident that conventional anticoagulant treatment for decreasing thrombogenicity does not effectively inhibit stenosis. That is, reduction in stenosis is not apparent or obvious from a decrease in thrombogenicity.

Other proposed drug treatments include agents that block the platelet receptor known as glycoprotein IIb/IIIa. One such agent designated CENTORX™ antibody to GP2a,3a (also known as 7E3) is described in *The New England Journal of Medicine*, Apr. 7, 1994, and *The Lancet*, Apr. 9, 1994. Other antithrombotics, e.g. NOVASTAN™ argatroban described in U.S. Pat. No. 4,248,192, and HIRULOG™bivalirudin, an analog of hirudin, also have been proposed for preventing restenosis. U.S. Pat. No. 5,308,622 describes the use of a conjugate of basic fibroblast growth factor (bFGF) and saporin (a ribosome inactivating agent) for preventing restenosis.

It is known that plasma contains a multivalent Kunitz-type inhibitor of coagulation, referred to herein as tissue factor pathway inhibitor (TFPI). This name has been accepted by the International Society on Thrombosis and Hemostasis, Jun. 30, 1991, Amsterdam.

TFPI was first purified from a human hepatoma cell, Hep G2, as described by Broze and Miletich, *Proc. Natl. Acad. Sci. USA* 84, 1886–1890 (1987), and subsequently from human plasma as reported by Novotny et al., *J.Biol.Chem.* 264, 18832–18837 (1989); and Chang liver and SK hepatoma cells as disclosed by Wun, et al., *J. Biol. Chem.* 265, 16096–16101 (1990).

TFPI cDNA have been isolated from placental and endothelial cDNA libraries as described by Wun et al., *J.Biol.Chem.* 263, 6001–6004 (1988); and Girard et al., *Thromb. Res.* 55, 37–50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus.

The first Kunitz-domain of TFPI is needed for the inhibition of the factor $VII_a$/tissue factor complex, and the second Kunitz-domain of TFPI is responsible for the inhibition of factor $X_a$ according to Girard et al., *Nature* 328, 518–520 (1989), while the function of the third Kunitz-domain remains unknown. See also U.S. Pat. No. 5,106,833.

TFPI is believed to function in vivo to limit the initiation of coagulation by forming an inert, quaternary factor $X_a$:

TFPI: factor VII$_a$: tissue factor complex. Further background information on TFPI can be found in reference to the recent reviews by Rapaport, Blood 73, 359–365 (1989); and Broze et al., *Biochemistry* 29, 7539–7546 (1990).

Recombinant TFPI has been expressed as a glycosylated protein using mammalian cell hosts including mouse C127 cells as disclosed by Day, et al., *Blood* 76, 1538–1545 (1990), baby hamster kidney cells as reported by Pedersen, et al., *J.Biol.Chem.* 265, 16786–16793 (1990), Chinese hamster ovary cells and human SK hepatoma cells. The C127 TFPI has been used in animal studies and shown to be effective in the inhibition of tissue factor-induced intravascular coagulation in rabbits according to Day, et al., supra.

TFPI has also been shown to prevent arterial reocclusion after thrombolysis in dogs by Haskel et al., *Circulation* 84, 821–827 (1991). However, the treatment with TFPI in the latter case involved initial artificial creation of a thrombus followed by recanalization with the clot dissolver, t-PA, in which the additional treatment with TFPI was observed only for the continued inhibition of thrombosis. Inhibition of thrombogenicity in such procedure does not, however, suggest reduction in stenosis following balloon angioplasty.

Recombinant TFPI also has been expressed as a non-glycosylated protein using *E. coli* host cells and obtaining a highly active TFPI by in vitro folding of the protein as described in U.S. Pat. No. 5,212,091, the disclosure of which is incorporated by reference herein. See also Wun, et al., *Thromb. Hemostas.* 68, 54–59 (1992); Diaz-Collier et al., *Ibid* 71, 339–346 (1994); and Gustafson et al, *Prot. Express. Purif.* 5, 233–241 (1994).

The cloning of the TFPI cDNA which encodes the 276 amino acid residue protein of TFPI is further described in Wun, et al., U.S. Pat. No. 4,966,852, the disclosure of which is incorporated by reference herein.

Recently, TFPI obtained through recombinant DNA clones expressed in *E. coli* as disclosed in U.S. Pat. No. 5,212,091 has been described as useful for reducing the thrombogenicity of microvascular anastomoses. See U.S. Pat. No. 5,276,015, the disclosure of which is incorporated herein by reference.

However, balloon angioplasty is not analogous to vascular anastomosis. They are two entirely different surgical procedures. Moreover, there is no suggestion that reduction of thrombogenicity in vascular anastomosis would have any effect on inhibition of stenosis in balloon angioplasty. Instead, it is evident from the art cited above that reduction in stenosis is neither apparent nor obvious from a decrease in thrombogenicity.

BRIEF DESCRIPTION OF THE INVENTION

In accordance with the present invention a novel method is provided for attenuating stenosis after balloon angioplasty. The method comprises prolonged treatment of a warm-blooded mammal following balloon angioplasty by administering parenterally or locally to the luminal surface of the blood vessel subjected to said balloon angioplasty an effective amount of tissue factor pathway inhibitor (TFPI) sufficient to reduce the extent of stenosis.

Because TFPI inhibits both factor $X_a$ elaborated by the complex of tissue factor and factor VII$_a$ as well as the activity of the complex, which is induced after injury to the vessel, TFPI is believed to have advantages over single site inhibitors including those for thrombin (the product of activation of prothrombin by factor $X_a$) or factor $X_a$. The results described herein show the unexpected advantage of TFPI compared with heparin for inhibition of stenosis after vessel injury.

The invention is illustrated in particular hereinbelow by the intravenous administration of recombinant TFPI after balloon hyperinflation-induced injury in the carotid artery of minipigs with hypercholesteremia induced by atherogenic diet. The results show in a large animal preparation of deep arterial injury simulating clinical angioplasty that recombinant TFPI (rTFPI) administered intravenously for 24 hours after vascular injury essentially abolishes subsequent formation of neointima and luminal stenosis.

In marked contrast, administration of rTFPI for only 3 hours did not reduce luminal stenosis one month later compared with heparin-treated control animals. Thus, inhibition of tissue factor mediated coagulation induced by initial exposure of tissue factor present in the vessel wall is insufficient to prevent the formation of neointima.

It will be appreciated that although the method of the invention is illustrated in particular hereinbelow with the minipig species, it is also useful for other warm-blooded mammals, e.g., humans, in an analogous manner.

Although the invention is illustrated in detail herein by i.v. administration of the TFPI, it will be appreciated that the TFPI can also be administered locally by any device suitable to apply the drug to the interior or luminal surface of the treated blood vessel, e.g., by a catheter-based delivery system. It can also be used in conjunction with a mechanical device used to prevent restenosis such as a stent, which can be a flexible cylinder, coil or slotted tube implanted at the time of angioplasty.

As defined herein, TFPI can be either glycosylated or non-glycosylated.

DETAILED DESCRIPTION OF THE INVENTION

While the specification concludes with claims particularly pointing out and distinctly claiming the subject matter which is regarded as forming the invention, it is believed that the invention will be better understood from the following detailed description of preferred embodiments of the invention taken in conjunction with the accompanying drawings in which:

FIG. 4 is 60 power.

FIGS. 9A and 9B, is a graphical representation which shows the effects of 24 hour intravenous infusions of anticoagulants on coagulation indices measured serially in plasma. FIG. 9A, activated partial thromboplastin time (aPTT). FIG. 9B, prothrombin time (PT).

A bolus of heparin (200 U/kg was given to each animal immediately after placement of the arterial sheath and collection of the baseline (t=0) blood sample (15 min before the start of the infusion of other anticoagulants to prevent clot formation in the catheters. Arterial injury was induced 15 min after the start of the infusion of anticoagulants. Points represent the mean and SEM. Dosages of antithrombotic agents are shown in Table 1.

In order to illustrate the invention in greater detail, the following illustrative Examples using a hyperlipidemic minipig model was carried out. It will be appreciated, however, that the invention is not limited to this exemplary work or to the specific details set forth in these Examples.

EXAMPLE I

Materials and Methods

Recombinant TFPI in 300 mM arginine phosphate buffer at pH 7.2 was infused intravenously (0.5 mg/kg bolus followed by 6 mg/kg/hr) for three (3) hrs (n=7) or for 24 hrs (n=7) after balloon hyperinflation-induced injury in the carotid arteries of minipigs with hypercholesteremia induced by atherogenic diet, which is a procedure that rapidly yields complex plaque-like lesions as reported previously in rabbits by Stevens et al., *Ann. of Vascular Surgery* 6, 55–61 (1992). After four (4) weeks, the injured vessels were perfusion fixed in situ and examined histologically.

The TFPI used in the foregoing Example was obtained through recombinant DNA clones expressed in *E. coli*. It is a 277-amino acid protein consisting of the 276 residue sequence described by Wun, et al., *J. Biol. Chem.* 263, 6001–6004 (1988), and in U.S. Pat. No. 4,966,852, with an additional alanine residue inserted at the N-terminus as described in U.S. Pat. No. 5,212,091. Unfractionated heparin was purchased from Elkins-Sinn, Cherry Hill, N.J.

Results

Figure 1:
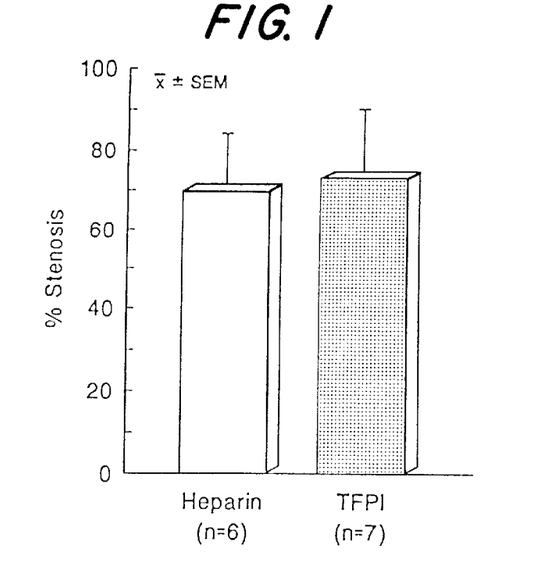
FIG. 1 is a bar graph which shows stenosis (in percentage) of the carotid arterial lumen four (4) weeks after balloon hyperinflation-induced injury in minipigs given intravenous infusions for three (3) hours of either heparin (100 U/kg/h) or. TFPI (0.5 mg/kg bolus and 6 mg/kg/h) beginning at the time of vessel injury.
Figure 2:
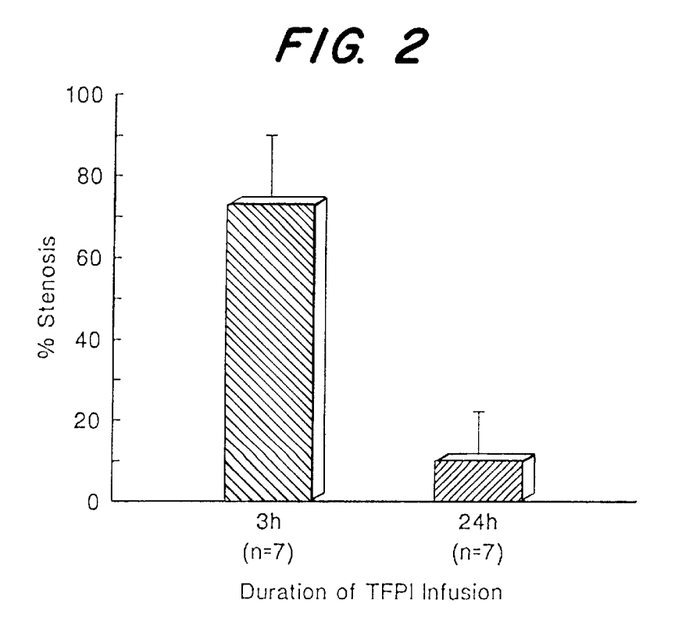
FIG. 2 is a bar graph which compares stenosis (in percentage) of the carotid artery four (4) weeks after balloon-induced injury in minipigs given TFPI as an intravenous infusion (0.5 mg/kg bolus and 6 mg/kg/h) for either three (3) hours or 24 hours.
Figure 4:
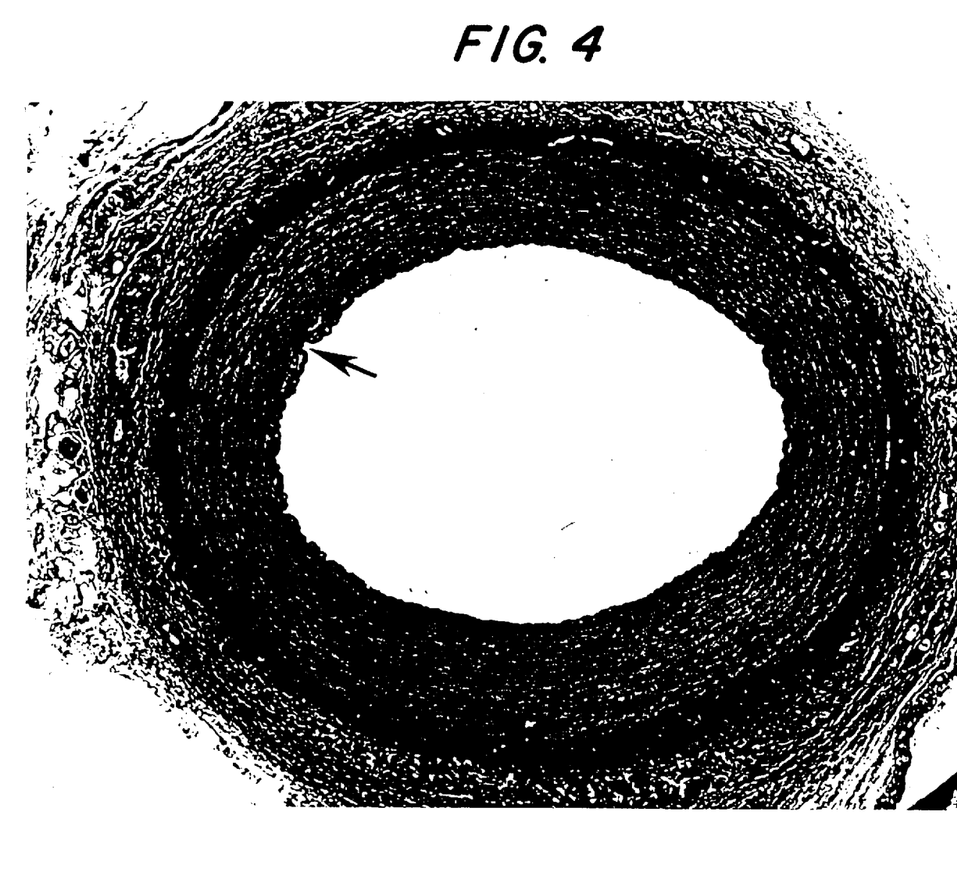
FIG. 4 is a photomicrograph of a carotid cross-section stained with Verhoeff's Van Gieson stain for elastic tissue obtained four (4) weeks after balloon injury in a minipig given TFPI for 24 hours. Despite the break in the internal elastic lamina (arrow), indicative of severe vessel injury, there is minimal proliferation of the intima and no visible thrombus on the luminal surface.

Histological examination of the above-treated vessels revealed that luminal stenosis was 73±13 (SE) % in minipigs given TFPI and 70±14% for those given heparin for three (3) hours (FIG. 1, p=NS). Stenosis was only 13±12% in minipigs given TFPI for 24 hours (FIG. 2, p=0.008 compared with three (3) hours of TFPI). Intimal lesions in animals receiving TFPI for 24 hours were negligible despite severe vessel injury indicated by rupture of the internal elastic lamina (FIG. 4).

Figure 3:
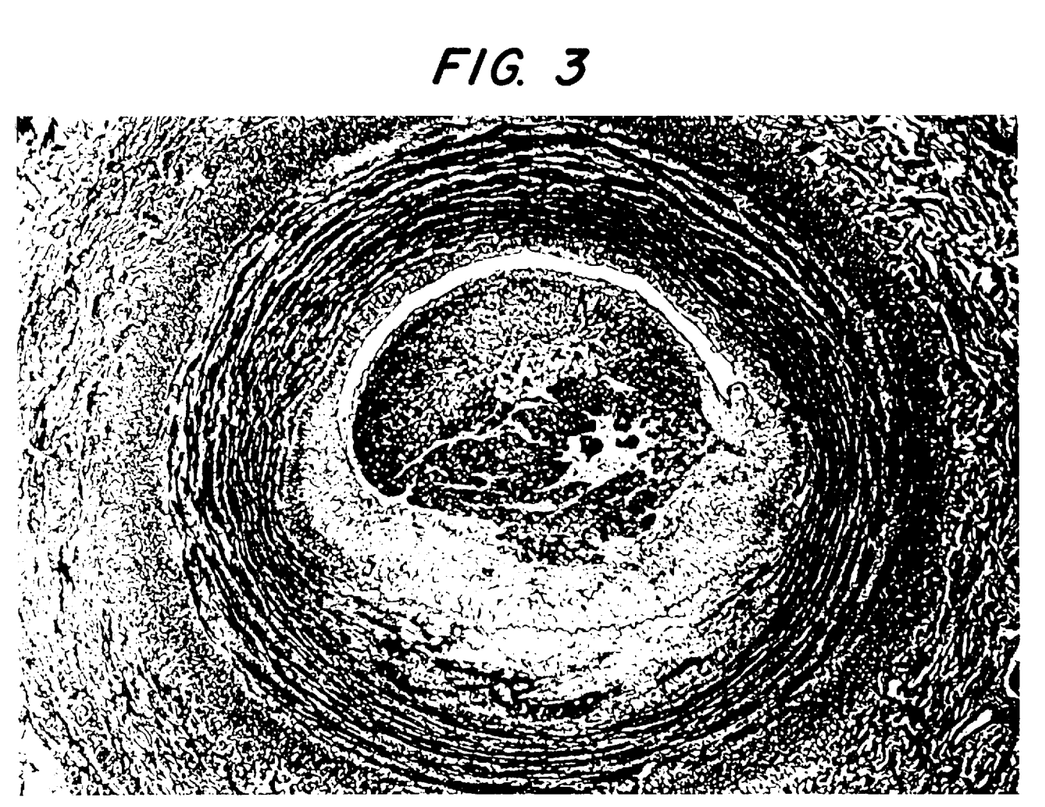
FIG. 3 is a photomicrograph of a carotid arterial cross-section stained with Masson's trichrome for collagen obtained four (4) weeks after balloon-induced injury in a minipig given heparin. Stenosis of the lumen is ≧80% with the intimal lesion comprised of a fibrous cap containing smooth muscle cells, a core of organizing thrombus, and foam cells at the base of the lesion. Severe damage to the media is evident by replacement of smooth muscle cells with collagen. The magnification in FIG. 3
Figure 5:
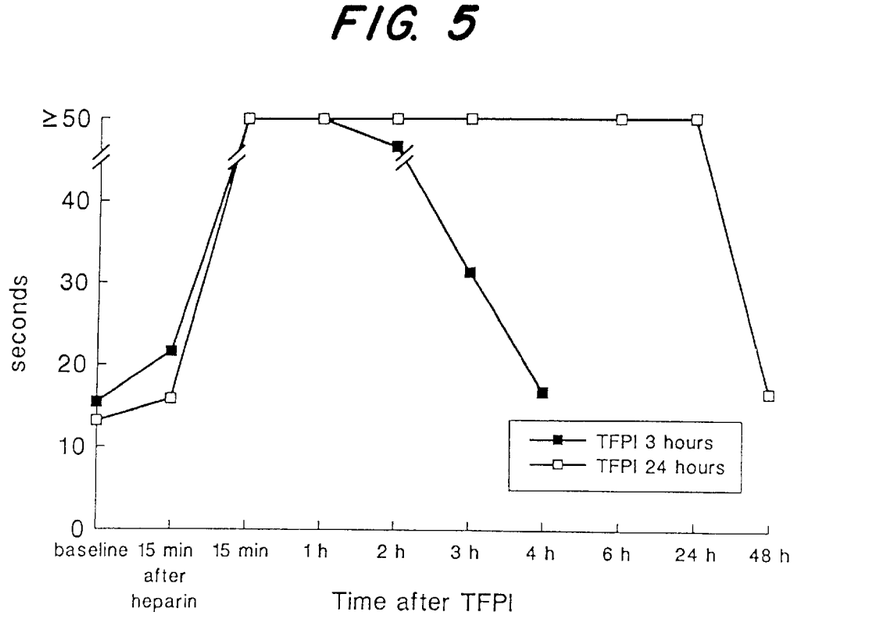
FIG. 5 is a graphical representation which shows the prothrombin time (PT) in minipigs given TFPI. The PT was ≧50 seconds (the maximum reading on the coagulation timer) throughout the infusion.
Figure 6:
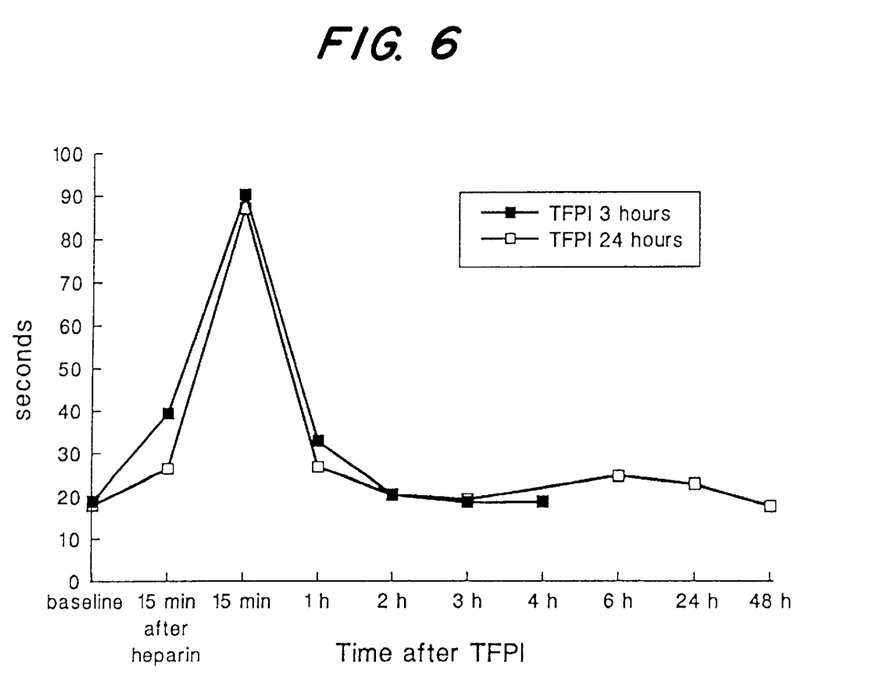
FIG. 6 is a graphical representation which shows the activated partial thromboplastin time (aPTT) in minipigs given TFPI. The early increase reflects intravenous injection of heparin given to prevent clot formation in the catheters before administration of TFPI. After heparin cleared from the circulation, but during continued infusion of TFPI, aPTT returned to baseline.

Adherent thrombus and foam cells observed in heparin-treated animals (FIG. 3) were also negligible in those given TFPI for 24 hours. Prothrombin time (PT), which evaluates the extrinsic pathway of coagulation by addition of tissue factor and calcium to a sample of plasma with measurement of the time of clot formation as the endpoint, was >2.5-fold baseline throughout the infusion of TFPI (FIG. 5). However, no changes in activated partial thromboplastin time (aPTT), which measures the intrinsic pathway of coagulation, were observed (FIG. 6). Thus, a 24-hr, but not a 3-hr infusion of TFPI markedly attenuated stenosis after balloon-induced arterial injury. These data indicate that TF-mediated thrombosis plays a role in the stenosis of injured vessels and that its prolonged inhibition can limit restenosis after balloon angioplasty.

EXAMPLE II

Methods

Animal Preparations

Procedures involving animals were conducted according to the guiding principles of the American Physiological Society and were approved by the Animal Studies Committee at Washington University. Male, three- to four-month old Yucatan minipigs (Charles River Laboratories, Wilmington, Mass.) weighing 16 to 18 kg were fed an atherogenic diet containing 4% cholesterol and 30% fat (Purina Test Diet 5748 M-A, Richmond, Ind.) [Recchia et al., *Atheroscler. Thromb. Vasc. Biol.* 15, 924–929 (1995)].

After verification that serum cholesterol levels had exceeded 300 mg/dl (generally observed 2 weeks after the start of the atherogenic diet), the pigs were sedated with an intramuscular cocktail of ketamine (22 mg/kg), acepromazine (1.1 mg/kg), and atropine (0.05 mg/kg). An ear vein was cannulated for administration of fluids and for induction of anesthesia with pentobarbital (20 mg/kg). The external jugular veins were exposed bilaterally with use of aseptic surgical techniques and catheters were placed in each and advanced into the vena cava for infusion of anticoagulant agents and for collection of blood samples. The trachea was intubated, but the pigs were allowed to breathe spontaneously unless ventilation became depressed. A femoral artery was exposed, an 8 F catheter sheath was inserted, and a bolus of heparin (200 U/kg) was administered intravenously to prevent clot formation in the catheters.

Test Protocol

The pigs were randomly assigned to one of six intravenous antithrombotic regimens (Table 1): high dose rTFPI for 3 or 24 hours; or, as control groups, additional heparin for 3 hours or 24 hours with or without aspirin. Recombinant TFPI was the full-length, 34 kD protein derived from *E. coli* [Gustafson et al., *Prot. Express. Purifica.* 5, 223–241 (1994)].

The high dose of rTFPI (100 $\mu$g/kg/min) was chosen because it inhibited tissue factor-mediated thrombosis associated with reocclusion of coronary arteries after fibrinolysis in dogs [Abendschein et al., *Circulation* 92, 944–949 (1995)]. The lower dose of rTFPI (25 $\mu$g/kg/min) was selected to determine whether stenosis could be inhibited with minimal perturbation of systemic hemostasis.

Fifteen minutes after the start of the infusion of antithrombotic agents, a 100 cm×6 F vertebral artery catheter (Softouch®; Mallinckrodt Inc., St. Louis, Mo.) was introduced through the femoral sheath, advanced under fluoroscopic guidance into the left carotid artery, and a baseline angiogram was obtained.

A balloon catheter (Proflex 5; 8 mm×2 cm Mallinckrodt Inc., St.. Louis, Mo.) was then advanced into the left carotid artery to the level of the second and third cervical vertebrae and the balloon was inflated five times to a distending pressure of 8 atmospheres for 30 sec with 60 sec between inflations, which has been shown to induce rupture of the internal elastic lamina and deep injury to the media [Recchia et al., supra; Steele et al., *Circ. Res.* 57, 105–112 (1985)].

Radiograms obtained during balloon inflations were compared with the baseline angiograms to measure the ratio of diameters of the balloon to the vessel as an index of the adequacy of vascular injury. After removal of the balloon catheter, another angiogram was obtained to verify patency of the injured carotid. The catheter sheath was then removed, the femoral artery was occluded, and the animals were recovered from anesthesia.

Patency of the injured vessel was assessed after 48 hours by transcutaneous ultrasound (Hewlett-Packard Sonos 1500 scanner with a 7.5 MHz linear array transducer, Andover, Md.). One month after balloon-induced injury, patency was reassessed angiographically and the arteries were prepared for analysis of luminal stenosis as described below.

Hematologic Assays, Bleeding Time, and Blood Levels of rTFPI and Cholesterol

Venous blood samples were obtained for analysis of activated partial thromboplastin time (aPTT), prothrombin time (PT), and rTFPI levels before the bolus of heparin (baseline), and serially for up to 48 hours after the start of infusions of additional anti-thrombotic agents.

Bleeding time and hematocrit were measured at baseline and 3 hours and 24 hours after the start of infusions of antithrombotic agents. Serum cholesterol levels were measured in the fasted animals before the start of the atherogenic diet, at the time of balloon-induced carotid injury and 4 weeks after balloon injury.

aPTT and PT were measured in citrated plasma with a manual method described previously [Brown, B.A., *Hematology, Principles and Procedures,* 4th Edition, 1984, Lea & Febiger, Philadelphia], because the turbidity in some samples caused by hyperlipemia interfered with conventional, automated assays.

Briefly, after the reagents for assay of PT (0.1 ml of SIMPLASTIN EXCEL™ thromboplastin reagent from rabbit brain, Organon Teknika, Durham, N.C.) or aPTT (0.1 ml of Automated aPTT Reagent and 0.1 ml of $CaCl_2$, Organon Teknika) were added to 0.1 ml of plasma, a 20 gauge needle with a small burr on the tip was slowly dipped and withdrawn repetitively from the solution until a strand of fibrin was observed attached to the needle.

The time from addition of reagent to the first appearance of the fibrin strand was taken as the clotting time. Results with the manual and automated (Coag-A-Mate XM®, Organon Teknika) methods applied to normolipemic samples were comparable (manual PT 14.3±0.3 sec, automated PT 13.2±0.3 sec, n=6; manual aPTT 14.5±0.7 sec, automated aPTT 18.6±0.3 sec, n=6).

Bleeding time was measured by the methods of Sawada et al., *Blood* 67, 1229–1239 (1986). Briefly, an incision was made through the edge of the ear near the apex using a No. 10 Bard-Parker blade. Care was taken to avoid the central ear artery and visible veins on the posterior surface of the ear.

The width of the incision was controlled by inserting the blade perpendicular to the ear to a depth of 5 mm. The ear was immersed in a beaker of isotonic saline that had been warmed to 37° C., and the time elapsed between the puncture and the cessation of any visible flow of blood from the incision was considered as the bleeding time.

Hematocrit was measured with a conductivity analyzer (Nova Biomedical, Waltham, Mass.). Recombinant TFPI levels in plasma were assayed by a particle concentration fluorescence immunoassay described previously [Abendschein et al., *Circulation* 92, 944–949 (1995)]. Serum cholesterol was measured spectrophotometrically at 37° C. with a coupled enzyme system (AC5–12) reagent, Schiapparelli Biosystems, Inc., Fairfield, N.J.) and a Gemeni centrifugal analyzer (Schiapparelli).

Analysis of Luminal Stenosis

Four weeks after balloon-induced carotid injury, the region of the injured artery with the smallest apparent luminal diameter was identified angiographically and its location marked on the skin. Both carotid arteries were perfused in situ with 500 ml of 0.9% NaCl followed by 500 ml of 4% paraformaldehyde at a constant pressure of 120 mm Hg via the 6 F angiographic catheter positioned proximally in the brachiocephalic artery.

The carotid arteries were then excised and 1 cm segments from the site of stenosis identified angiographically and from a similar location in the contralateral, uninjured artery as a control were immersion fixed in 4% paraformaldehyde for 24 hours, embedded in paraffin, cut through their entirety at a thickness of 5 μm, and sets of sections collected every 100 μm were stained with hematoxylin and eosin and with Verhoeff's Van Gieson stain for elastic tissue.

The extent of luminal stenosis was assessed with the investigators blinded to the treatment group. Low power microscopic images of sections exhibiting the smallest luminal diameters and stained for elastic tissue (to facilitate identification of the internal elastic lamina) were digitized with use of a Nikon Optiphot-2 microscope with a CCD camera attached to a Macintosh IIci computer outfitted with a NuVista frame-grabber board.

The cross-sectional areas of the lumen and neointima were planimetered by tracing the margin of the lumen and internal elastic lamina. Percent luminal obstruction was then calculated as 1 minus the area of the lumen divided by the area within the internal elastic lamina multiplied by 100.

Analysis of rTFPI Pharmacokinetics in vivo

In two additional cholesterol-fed, anesthetized minipigs, rTFPI was administered as an intravenous bolus (0.5 mg/kg) and blood samples were obtained serially for assay of plasma levels. Data from each animal were analyzed by non-linear regression and the modified Gauss-Newton method of residuals in which exponential terms are sequentially peeled off. Data from individual animals fit consistently to a bi-exponential of the form:

$$C = Ae^{-at} + Be^{-bt}$$

where C is the concentration of rTFPI at time t (min), and A and B are intercept values (t=0) extrapolated from a and b, the first order elimination constants.

Statistical Analysis

Results are expressed as mean ±SEM. ANOVA with a repeated measures design was used to assess time-dependent changes in hemostatic variables and cholesterol levels. A Wilcoxon test was used to compare the severity of luminal stenosis between treatment groups. A value of $p \leq 0.05$ was considered significant.

RESULTS

Fifty-two animals were subjected to the carotid injury procedure. Thirteen (25%) were excluded; nine died after the carotid artery injury (eight had been treated with heparin or the combination of heparin and aspirin and appeared to succumb to bleeding complications); two did not exhibit persistent elevations of serum cholesterol >300 mg/dl over the 4 weeks after arterial injury; and two did not exhibit disruption of the internal elastic lamina at the site of previous balloon injury.

None of the remaining 39 animals that completed the protocol exhibited occlusion of the injured carotid artery assessed ultrasonically after 48 hours or angiographically after 4 weeks. However, each of these animals was confirmed to have multiple and extensive disruptions of the internal elastic lamina at the site of previous balloon-induced carotid injury. The balloon/vessel ratio averaged 1.20±0.06 (n=27) and was not different between treatment groups.

Mean serum cholesterol levels were significantly increased in the six treatment groups at the time of balloon-induced arterial injury and 4 weeks later compared with baseline values (Table 2). However, the levels did not differ between groups.

Luminal Stenosis

Figure 7:
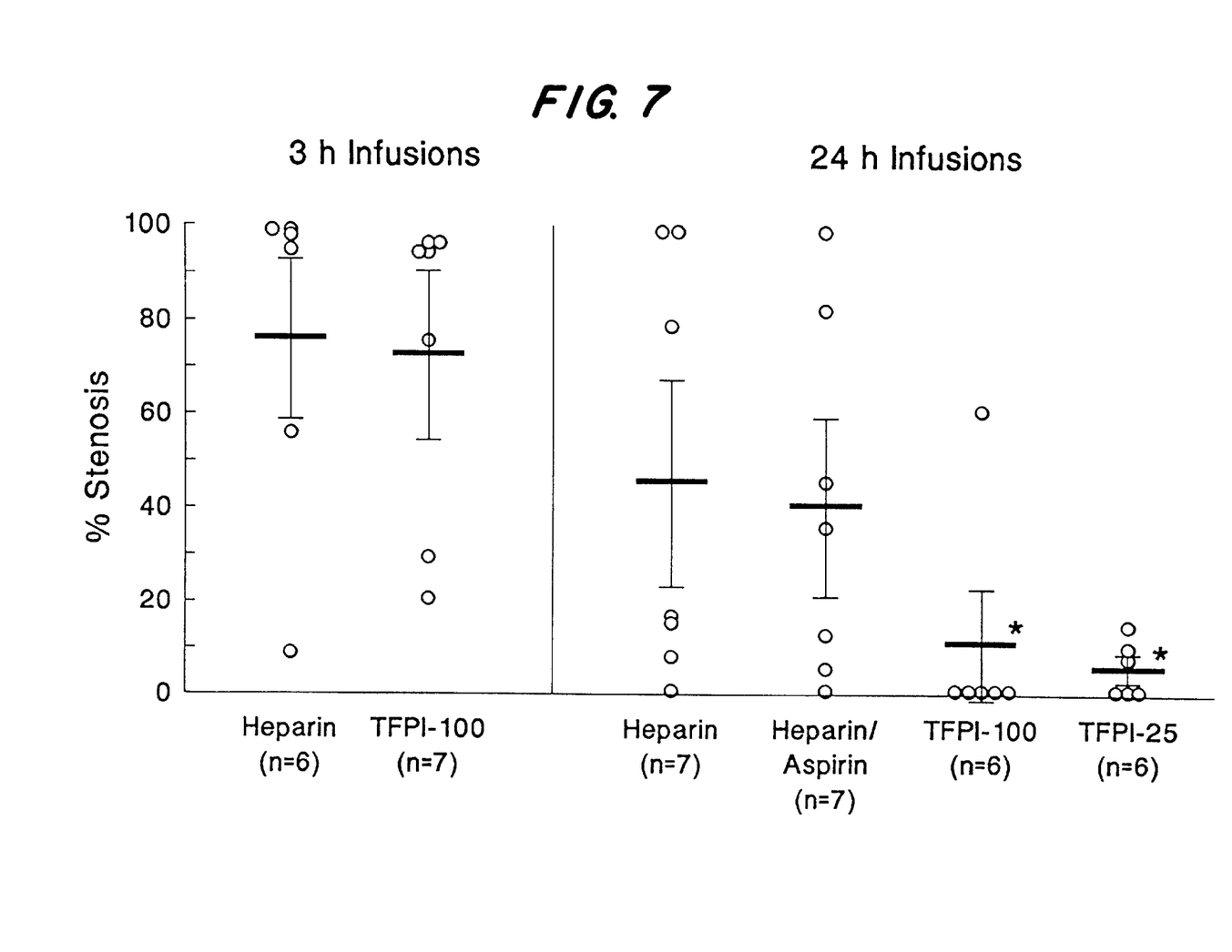
FIG. 7 is a plot which shows the effects of antithrombotic agents administered for either 3 hours or 24 hours after balloon-induced injury to the carotid artery on the percent luminal stenosis measured histologically four (4) weeks later. Results for each animal are shown as open circles. Horizontal lines represent the mean and SEM *$p<0.0002$ compared with all other treatments. Dosages are defined in Table 1.

Administration of the high dose of rTFPI or heparin for three hours after balloon-induced carotid arterial injury was associated with marked luminal stenosis four weeks later that did not differ between groups (73±17% for rTFPI and 76±18% for heparin) (FIG. 7).

Figure 8A:
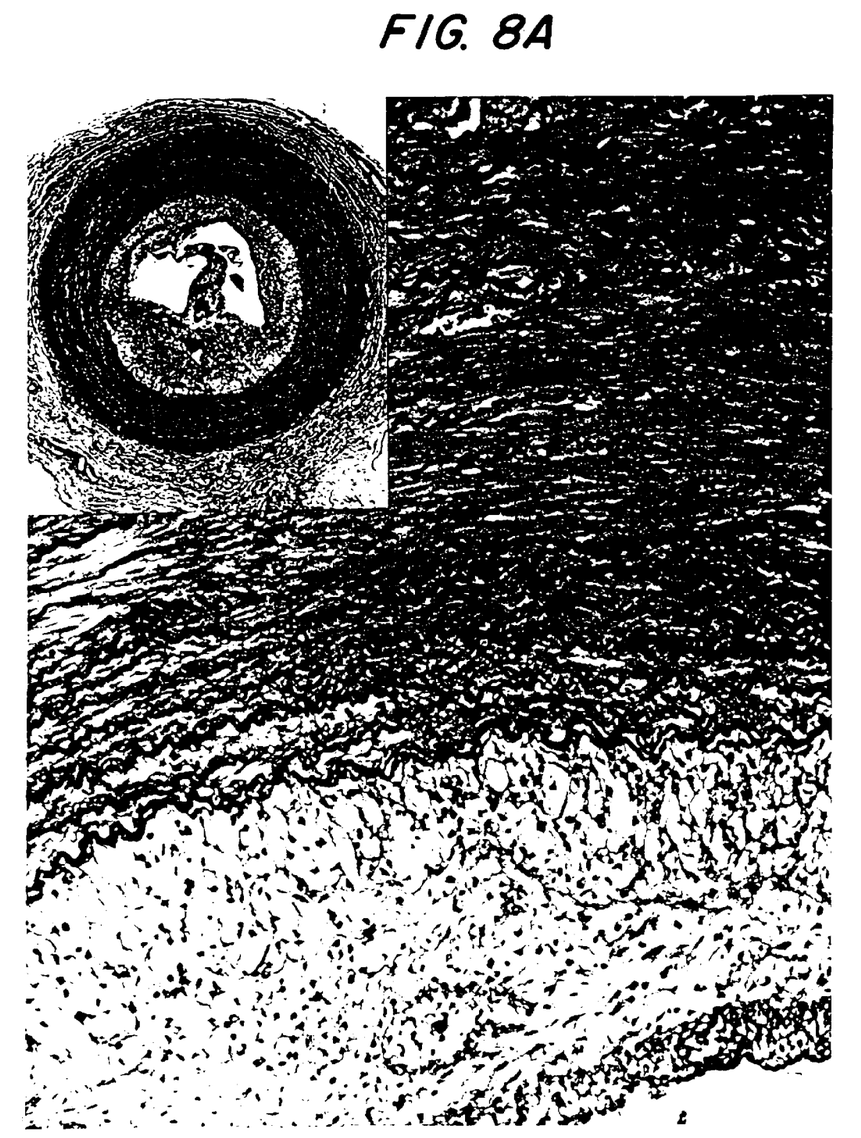
FIGS. 8A and 8B, shows photomicrographs of carotid arterial cross-sections obtained from pigs that received either heparin (FIG. 8A) or the high dosage of rTFPI (FIG. 8B), for 24 hours after balloon-induced injury. Sections were stained with Van Geison's stain for elastic tissue to identify the internal elastic lamina and disruptions in the lamina that indicated deep injury to the arterial wall (arrow). Neointima nearly filled the lumen of the heparin-treated vessel (inset to FIG. 8A), but comprised a thin layer despite multiple breaks in the internal elastic lamina in the rTFPI-treated vessel.
Figure 8B:
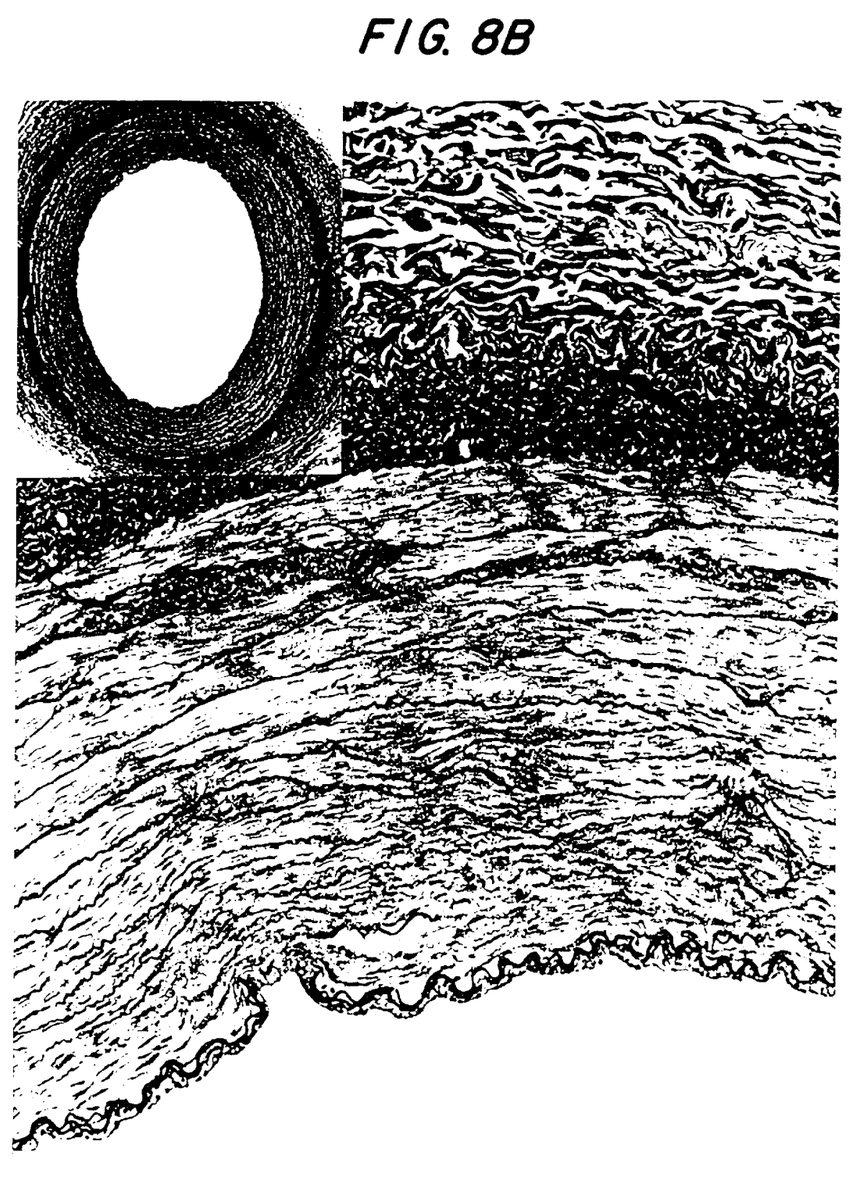

Treatment for 24 hours with heparin (46±22%) or the combination of heparin and aspirin (40±19%) resulted in modest but insignificant reductions in luminal stenosis compared with 3 hours administration of agents (FIGS. 7 and 8).

However, 24 hour administration of both high and low doses of rTFPI was associated with significant reductions in luminal stenosis (11±12% for the high dose and 6±3% for the low dose) compared with all other treatment groups (p<0.0002).

In fact, all but one pig given the high dose of rTFPI for 24 hours exhibited <1% luminal stenosis (FIGS. 7 and 8). The remaining animal had a stenosis of 61% resulting in a higher mean value for the group. Interestingly, the neointimal lesion in this animal was much different in appearance than the lesion from any other animal, exhibiting a loose connective tissue-like composition.

Hematologic Variables

Figure 9A:
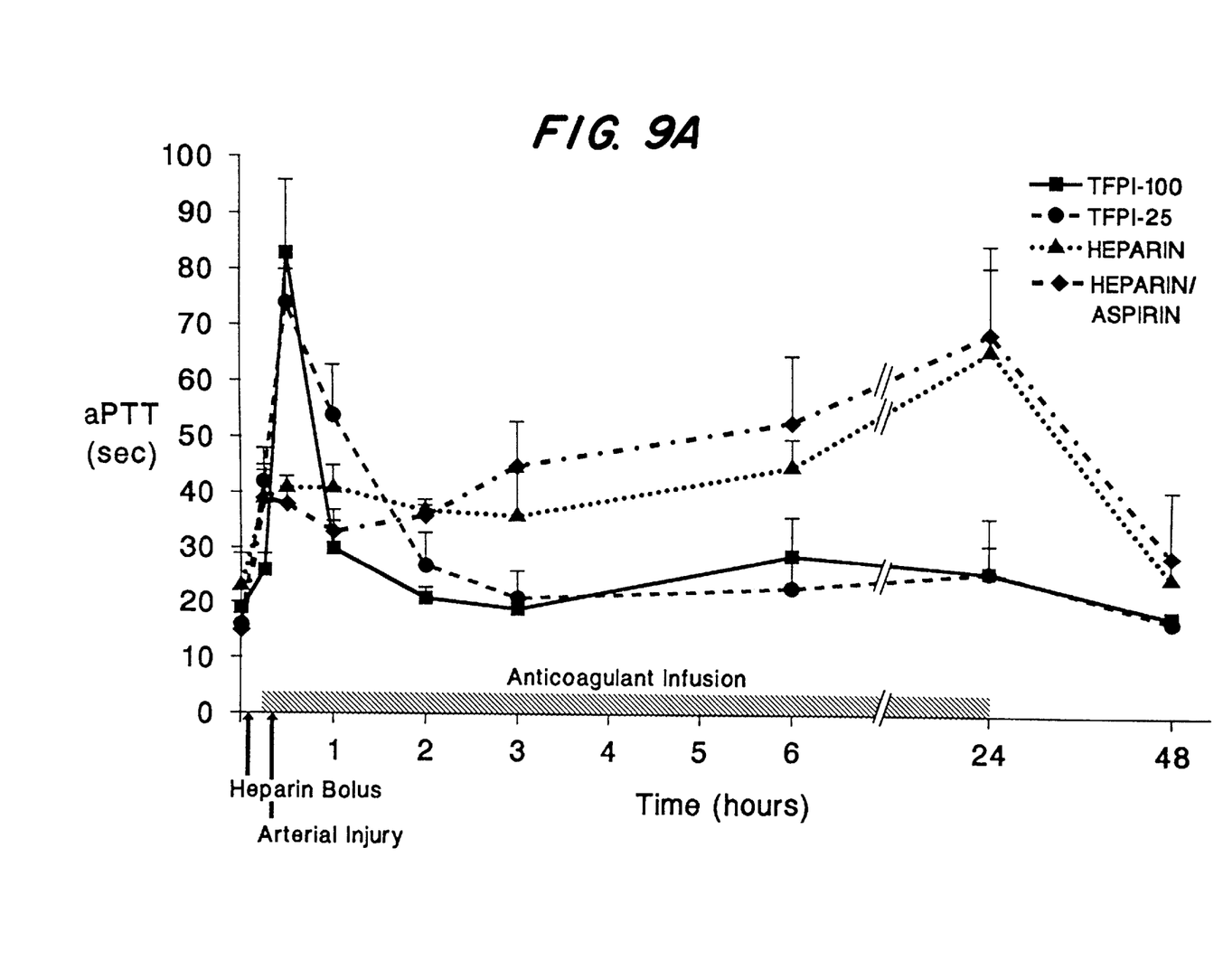
Figure 9B:
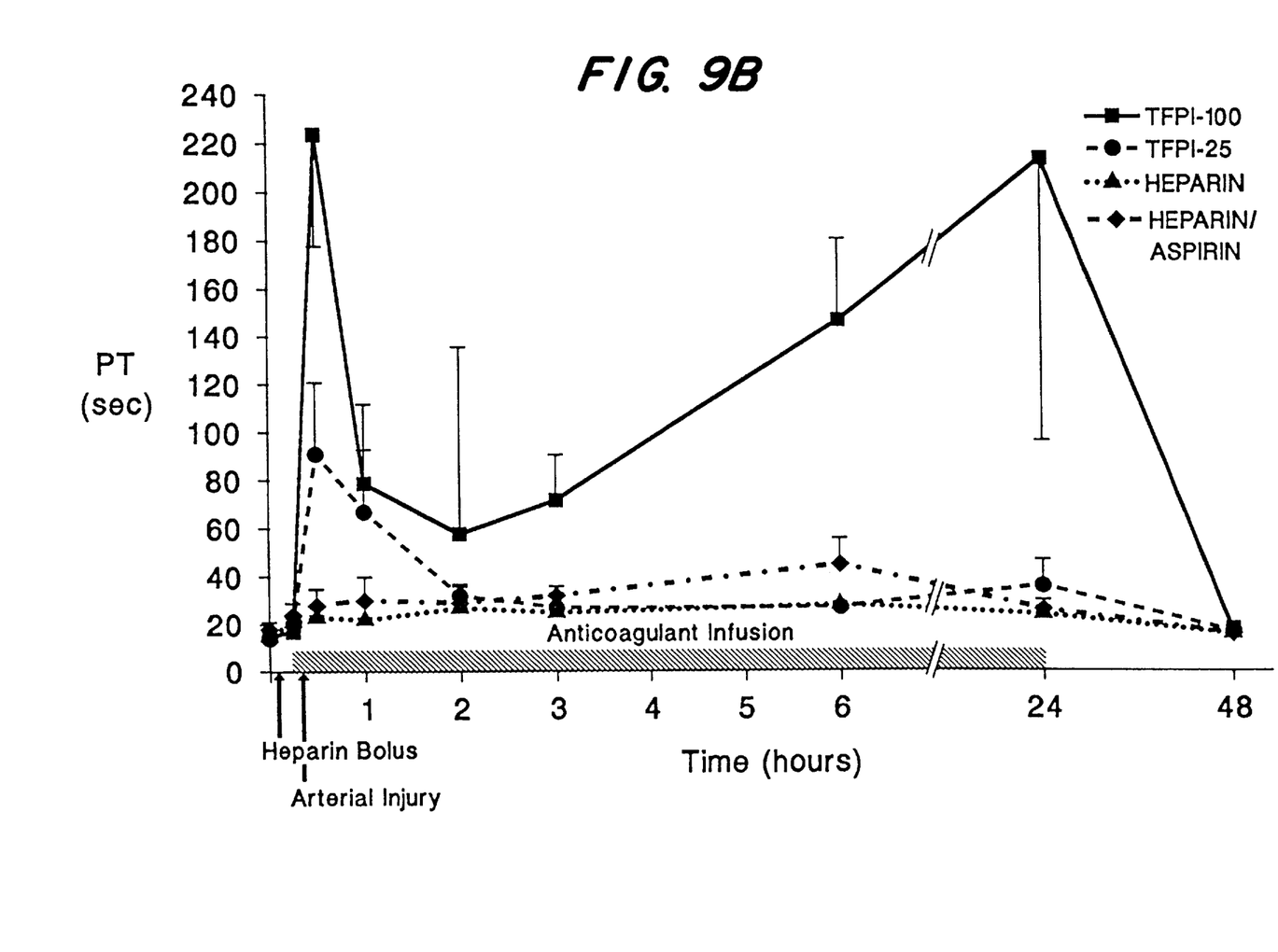

Plasma aPTT and PT levels in animals given 24 hour infusions of antithrombotic agents are shown in FIG. 9. Similar data were obtained in animals treated with rTFPI or heparin for 3 hours. In contrast, aPTT remained 2- to 4-four fold above baseline levels throughout the administration of heparin or heparin and aspirin (p<0.001).

PT was also increased over the first hour after the bolus of rTFPI (p<0.01). It returned to baseline within the second hour in animals given the low dose infusion of rTFPI, but exhibited a second, progressive rise beginning at 3 hours (p<0.02) to >10-fold baseline during infusion of the high dose. PT was not increased significantly in heparin-treated animals.

Figure 10:
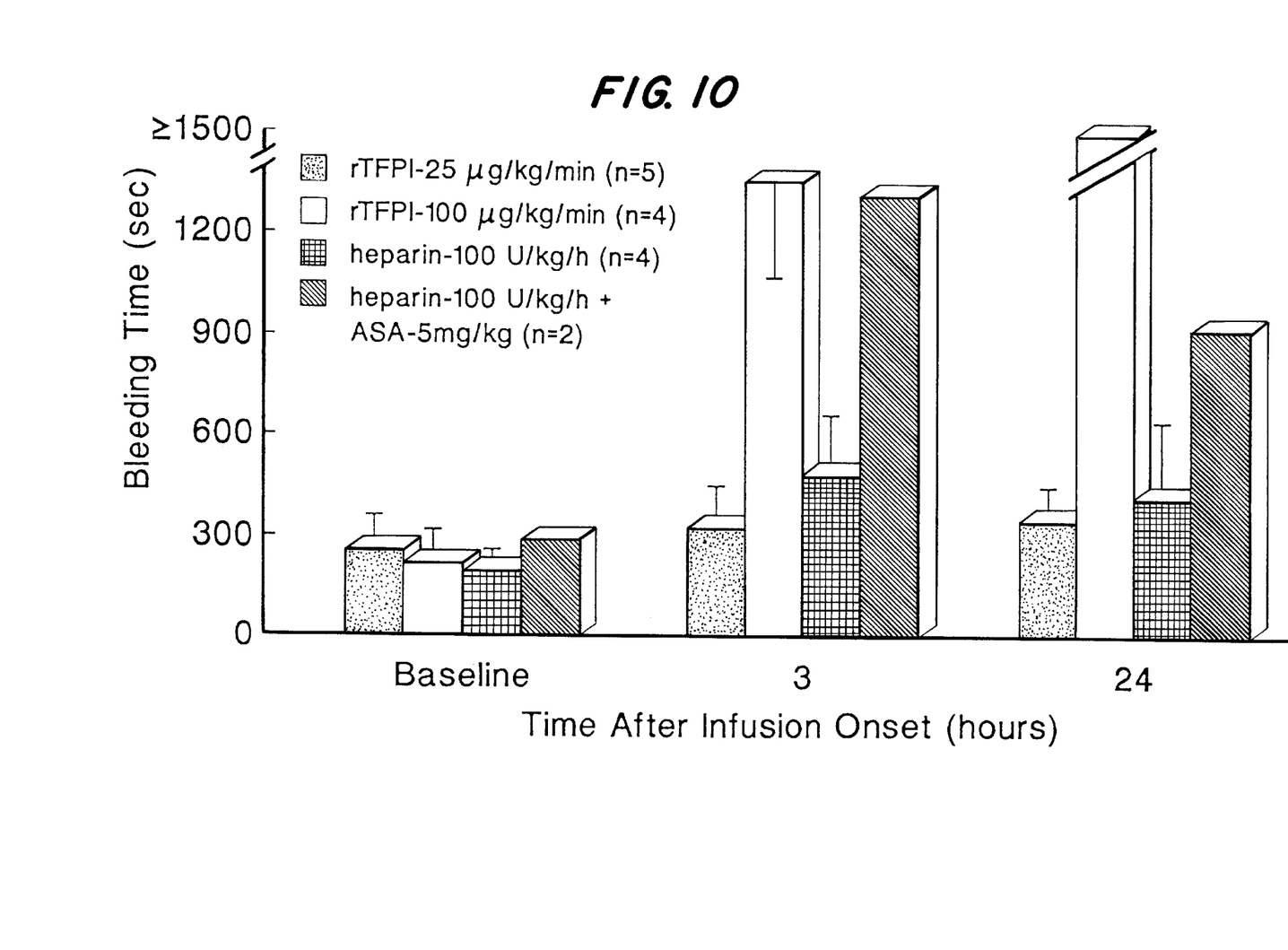
FIG. 10 is a bar chart which shows the effects of antithrombotic agents on the time of bleeding from a deep incision to the edge of the ear. Bars represent the mean and SEM. The maximal value recorded was 1500 sec. The high dosage of rTFPI resulted in a significant increase of bleeding time compared with values at baseline ($p<0.001$). The combination of heparin and aspirin also increased bleeding, but limited data precluded a statistical comparison in this test.

Bleeding time increased markedly compared with baseline in animals given the high dose of rTFPI (p<0.001) and in those given the combination of heparin and aspirin (FIG. 10). Bleeding time was not increased significantly in animals given either the low dose of rTFPI or heparin alone. Hematocrit did not change over 48 hours in any of the treatment groups.

rTFPI Pharmacokinetics and Blood Levels

Figure 11:
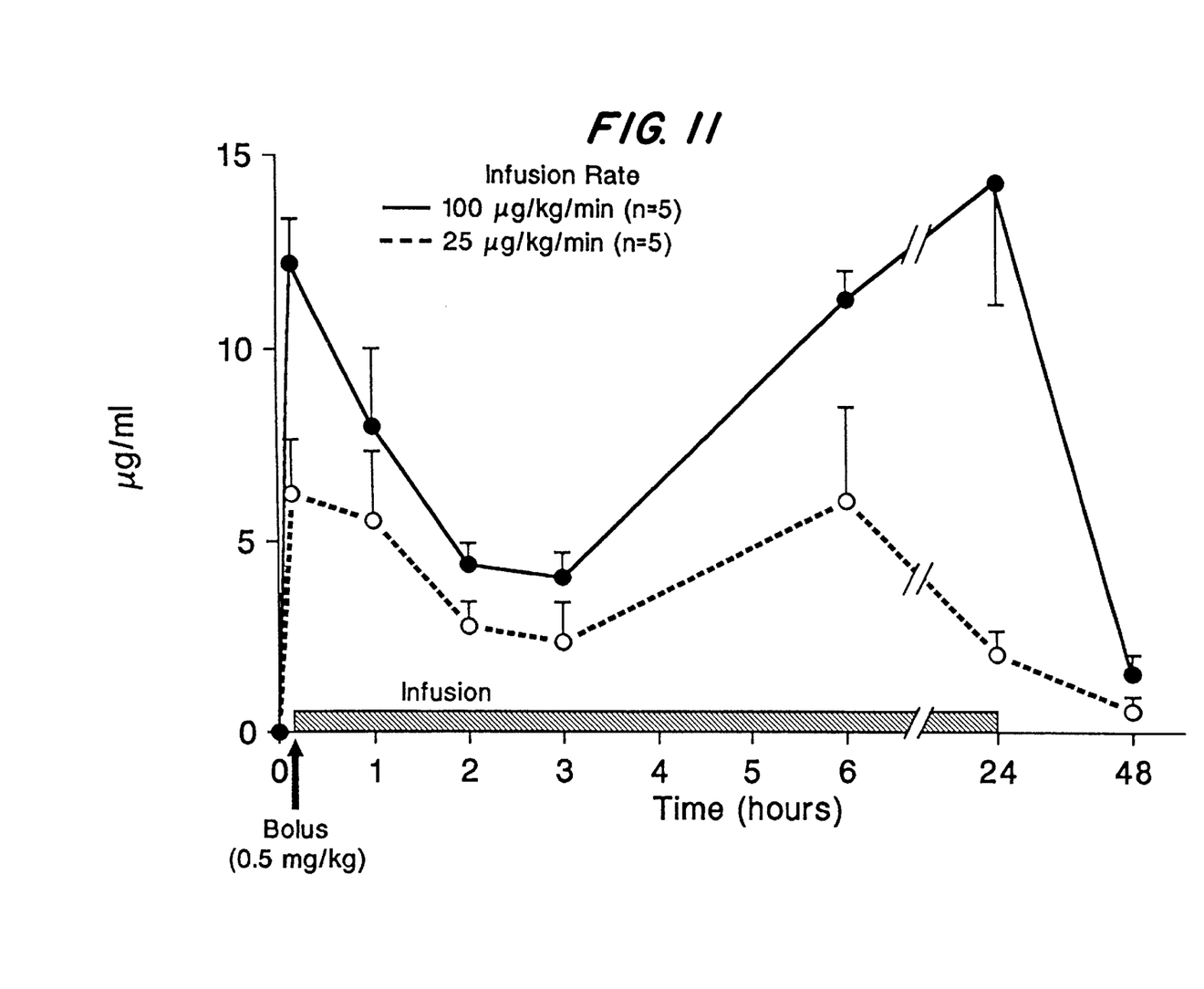
FIG. 11 is a graphical representation which shows the plasma levels of rTFPI in pigs that received a bolus followed by a 24-hour intravenous infusion of either a high or low dosage of rTFPI.

The average clearance of rTFPI following a bolus intravenous injection in two pigs was 8.6 ml/min/kg with a $t_{1/2}$ for the alpha phase of 1.3 min and a $t_{1/2}$ for the beta phase of 28.8 min. Plasma levels during constant intravenous infusions of rTFPI showed a time-dependent increase that reached an apparent maximum concentration of 6.0±4.9 g/ml after 6 hours in animals given the low dose and 14.3±6.2 μg/ml after 24 hours in animals given the high dose of rTFPI (FIG. 11).

TABLE 1

Antithrombotic Treatment Protocols

| Group | n* | Treatment** |
|---|---|---|
| TFPI-100/3 h | 8 | TFPI (O.5 mg/kg bolus, then 100 μg/kg/min infusion for 3 h) |
| TFPI-100/24 h | 7 | TFPI (0.5 mg/kg bolus, then I00 μg/kg/min infusion for 24 h) |
| TFPI-25/24 h | 7 | TFPI (0.5 mg/kg bolus, then 25 μg/kg/min infusion for 24 h) |
| Hep/3 h | 7 | Heparin (100 U/kg/h infusion for 3 h) |
| Hep/24 h | 10 | Heparin (100 U/kg/h infusion for 24 h) |
| Hep-ASA/24 h | 13 | Heparin (100 U/kg/h infusion for 24 h) and aspirin (5 mg/kg, PO) |

*number randomized
**each animal received 200 U/kg heparin 15 min before the onset of additional treatment

TABLE 2

Serum Cholesterol Levels*

| n | TFPI-100/3 h 7 | TFPI-100/24 h 6 | TFPI-25/24 h 6 | hep/3 h 6 | hep/24 h 7 | hep-ASA/24 h 7 |
|---|---|---|---|---|---|---|
| Baseline | 81 ± 5 | 67 ± 2 | 55 ± 2 | 89 ± 13 | 67 ± 6 | 59 ± 8 |
| Time of injury | 606 ± 127** | 601 ± 91** | 589 ± 151** | 80 ± 177** | 544 ± 118** | 667 ± 180** |
| 4 wk after injury | 761 ± 161** | 751 ± 42** | 592 ± 65** | 510 ± 101** | 518 ± 56** | 570 ± 100** |

*mg/dl
** = p<0.001 compared with baseline

The parenteral administration of the TFPI is preferably carried out by intravenous administration of the TFPI from admixture with a physiologically acceptable vehicle or carrier, e.g., normal saline or buffered saline such as phosphate buffered saline (PBS), arginine phosphate buffer or other such pharmaceutically acceptable buffers, e.g., HEPES.

Such conventional vehicles are well known, as can be seen by reference to numerous texts and treatises in the field of drug administration, e.g., *Remington's Pharmaceutical Sciences,* ed. Arthur Osol, 16th ed., 1980, Mack Publishing Co., Easton, Pa.

The amount of TFPI parenterally administered can vary widely, depending upon the degree or severity of the stenosis. Doses of from about 0.5 mg/kg to about 6.0 mg/kg per hr by prolonged administration of from twelve (12) to about 36 hrs are preferred. Intermittent bolus injections of TFPI in the range of 0.5 mg/kg to 1.0mg/kg, (or direct delivery of TFPI to the vessel with use of catheter-based drug delivery systems at critical intervals after induction of vascular injury) e.g., at zero (0) hrs and eight (8) hrs may reduce the total quantity of drug required.

Various other examples will be apparent to the person skilled in the art after reading the present disclosure without departing from the spirit and scope of the invention. It is intended that all such other examples be included within the scope of the appended claims.

What is claimed is:

1. A method for attenuating stenosis after balloon angioplasty in a mammal comprising administering parenterally or locally to the luminal surface of a blood vessel subjected to said balloon angioplasty an effective amount of Tissue Factor Pathway Inhibitor (TFPI) for a prolonged period of time sufficient to substantially reduce the extent of stenosis.

2. The method of claim 1 in which the TFPI is carried in normal saline buffered to physiological pH.

3. The method of claim 1 in which the TFPI is administered in an amount of from about 0.5 mg/kg to about 6 mg/kg per hour by prolonged administration of from about 12 to about 36 hours.

4. A method for reducing stenosis in a mammal caused by balloon angioplasty, comprising administering over a prolonged period of time an effective amount of TFPI to reduce said stenosis.

5. The method of claim 4 wherein said TFPI is administered parenterally.

6. The method of claim 4 wherein said TFPI is administered locally.

7. The method of claim 4 wherein said TFPI is carried by a physiologically acceptable vehicle.

8. The method of claim 4 wherein said TFPI is administered in an amount of from about 0.5 mg/kg to about 6 mg/kg per hour in said physiologically acceptable vehicle.

9. The method of claim 4 wherein said TFPI is (ala$^{-1}$)-TFPI (1–277) or native TFPI (1–276).

10. The method of claim 4 wherein said TFPI is the first and second Kunitz domain of said TFPI.

11. The method of claim 4 further comprising an additional alanine at the N-terminus of said TFPI.

12. The method of claim 4 wherein said TFPI is the first or second Kunitz domain of said TFPI.

13. The method of claim 4 wherein said prolonged period is from about 3 hours to about 24 hours.

14. The method of claim 4 wherein said prolonged period is from about 24 hours to about 1 week.

* * * * *